(12) United States Patent
Hurskainen et al.

(10) Patent No.: US 11,162,955 B2
(45) Date of Patent: Nov. 2, 2021

(54) SYSTEM AND METHOD FOR DETERMINING RISK OF DIABETES BASED ON BIOCHEMICAL MARKER ANALYSIS

(71) Applicant: Wallac Oy, Turku (FI)

(72) Inventors: Pertti Hurskainen, Piispanristi (FI); Teemu Korpimäki, Turku (FI); Heikki Kouru, Raisio (FI); Mikko Sairanen, Masku (FI)

(73) Assignee: Wallac Oy, Turku (FI)

( * ) Notice: Subject to any disclaimer, the term of this patent is extended or adjusted under 35 U.S.C. 154(b) by 299 days.

(21) Appl. No.: 16/145,650

(22) Filed: Sep. 28, 2018

(65) Prior Publication Data

US 2019/0137508 A1    May 9, 2019

Related U.S. Application Data

(62) Division of application No. 13/836,256, filed on Mar. 15, 2013, now Pat. No. 10,119,978.

(51) Int. Cl.
*G01N 33/68* (2006.01)

(52) U.S. Cl.
CPC ... *G01N 33/689* (2013.01); *G01N 2333/7151* (2013.01); *G01N 2333/8132* (2013.01); *G01N 2800/042* (2013.01); *G01N 2800/368* (2013.01); *G01N 2800/54* (2013.01)

(58) Field of Classification Search
None
See application file for complete search history.

(56) References Cited

U.S. PATENT DOCUMENTS

| | | | |
|---|---|---|---|
| 5,594,637 A | 1/1997 | Eisenberg et al. | |
| 10,119,978 B2 | 11/2018 | Hurskainen et al. | |
| 2005/0148023 A1 | 7/2005 | Thadhani et al. | |
| 2007/0178530 A1 | 8/2007 | Poston et al. | |
| 2007/0178543 A1 | 8/2007 | Self | |
| 2009/0247454 A1 | 10/2009 | Fernandez-Real Lemos et al. | |
| 2009/0318775 A1 | 12/2009 | Michelson et al. | |
| 2011/0294227 A1* | 12/2011 | Ahola | G01N 33/689 436/501 |
| 2012/0040846 A1 | 2/2012 | Kassis | |
| 2012/0053073 A1* | 3/2012 | Kassis | A61P 15/00 506/9 |
| 2014/0273024 A1 | 9/2014 | Hurskainen et al. | |
| 2018/0156815 A1 | 6/2018 | Hurskainen et al. | |

FOREIGN PATENT DOCUMENTS

| | | |
|---|---|---|
| CN | 102047255 A | 5/2011 |
| CN | 102224422 A | 10/2011 |
| WO | WO-2005/017192 A2 | 2/2005 |
| WO | WO-2010/059952 A1 | 5/2010 |
| WO | WO-2011/059720 A2 | 5/2011 |

OTHER PUBLICATIONS

Anderson, N. L., The Clinical Plasma Proteome: A Survey of Clinical Assays for Proteins in Plasma and Serum, Clinical Chemistry, 56(2):177-185 (2010).
Bellart et al., "Coagulation and Fibrinolysis Parameters in Normal Pregnancy and in Gestational Diabetes", American Journal of Perinatology/vol. 15, No. 8, Aug. 1998, 479-486, 8 pages.
Bryson, C. L. et al., Association between Gestational Diabetes and Pregnancy-induced Hypertension, American Journal of Epidemiology, 158(12):1148-1153 (2003).
International Search Report for PCT/IB2014/059278, dated Sep. 29, 2014, 6 pages.
Invitation to Pay Additional Fees with Partial International Search for PCT/IB2014/059278, 8 pages (dated Jul. 2, 2014).
Koh, S.C.L et al., The Influence of Labor and Placental Separation on Hemostasis in Term Pregnancy, Clinical and Applied Thrombosis/Hemostasis, 4:4:262-267, (1998).
Reith, A. et al, Plasminogen activator inhibitors (PAI-1 and PAI-2) in normal pregnancies, pre-eclampsia and hydatidiform mole, British Journal of Obstetrics and Gynecology, 100:370-374 (1993).
Robitaille, J. et al., The Genetics of Gestational Diabetes Mellitus: Evidence for Relationship with Type 2 Diabetes Mellitus, Genetics in Medicine, 10:4:240-250, (2008).
Winkler et al., "Tumor necrosis factor system in insulin resistance in gestational diabetes," Diabetes Research and Clinical Practice 56 (2002) 93-99, 7 pages.
Written Opinion for PCT/IB2014/059278, dated Sep. 29, 2014, 12 pages.
Kinalski, M. et al., Tumor Necrosis Factor Alpha System and Plasma Adiponectin Concentration in Women with Gestational Diabetes, Hormone and Metabolic Rese, 27(7):450-454 (2005).
Niewczas, M. A. et al., Circulating TNF Receptors 1 and 2 Predict ESRD in Type 2 Diabetes, Clinical Research, Journal of American Society Nephrology, 23(3):507-515 (2012).

* cited by examiner

Primary Examiner — Andrea S Grossman
(74) Attorney, Agent, or Firm — Choate, Hall & Stewart LLP; William R. Haulbrook; Meaghan E Bychowski

(57) ABSTRACT

A method for predicting risk of gestational diabetes mellitus (GDM) in a pregnant individual includes measuring one or more biochemical markers in a blood sample obtained from the pregnant individual to determine one or more biomarker levels, where the one or more measured biochemical markers includes at least one of PAI-2 and sTNFR1, identifying, for each of the one or more measured biochemical markers, a difference between the measured biomarker level and a corresponding predetermined control level, and, responsive to the identifying, determining a prediction corresponding to a relative risk of the pregnant individual having or developing GDM.

20 Claims, 9 Drawing Sheets

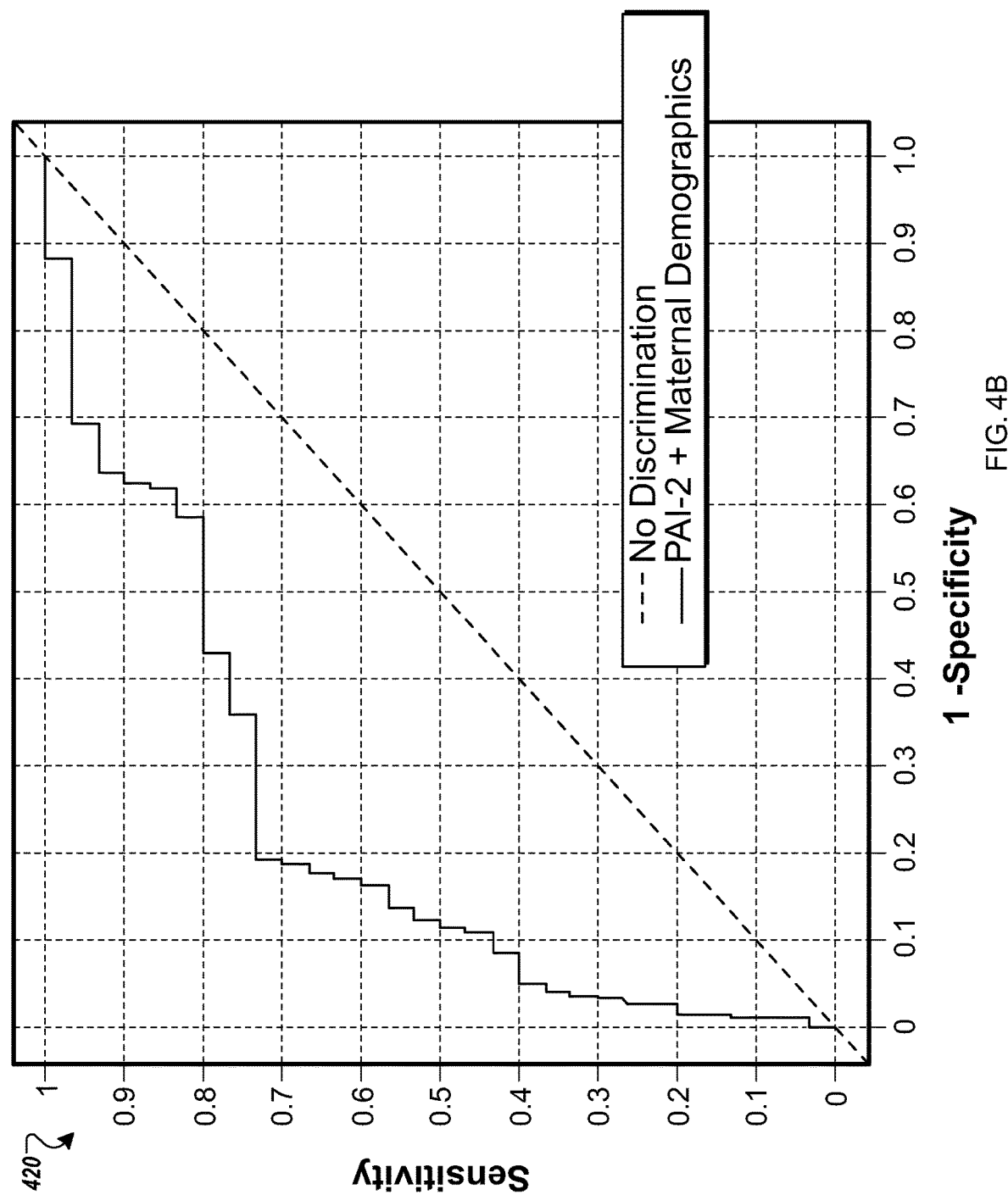

500

```
┌─────────────────────────────────────────────────────────────┐
│ Obtain Measurements from a Biological Sample of One or More │
│ Biomarker Levels Corresponding to One or More Biochemical   │
│ Markers, where the Biochemical Marker(s) Include at Least   │
│ One of PAI-2 and sTNFR1                                 502 │
└─────────────────────────────────────────────────────────────┘
                              │
                              ▼
┌─────────────────────────────────────────────────────────────┐
│ Identify, for Each of the One or More Biomarker Levels, a   │
│ Difference Between the Biomarker Level and a Corresponding  │
│ Predetermined Control Level                             504 │
└─────────────────────────────────────────────────────────────┘
                              │
                              ▼
┌─────────────────────────────────────────────────────────────┐
│ Access One or More Demographic Values Associated with the   │
│ Pregnant Individual                                     506 │
└─────────────────────────────────────────────────────────────┘
                              │
                              ▼
┌─────────────────────────────────────────────────────────────┐
│ Access One or More Biophysical Values Associated with the   │
│ Pregnant Individual                                     508 │
└─────────────────────────────────────────────────────────────┘
                              │
                              ▼
┌─────────────────────────────────────────────────────────────┐
│ Determine, Based in Part Upon the Difference(s) the         │
│ Biomarker Level(s) and the Corresponding Predetermined      │
│ Control Level(s) and, Optionally, One or Both of the        │
│ Demographic Value(s) and the Biophysical Value(s), a Risk   │
│ Assessment Score Corresponding to a Relative Risk of the    │
│ Pregnant Individual Having or Developing GDM            510 │
└─────────────────────────────────────────────────────────────┘
                              │
                              ▼
┌─────────────────────────────────────────────────────────────┐
│ Present, Upon the Display of a User Computing Device, the   │
│ Risk Assessment Score                                   512 │
└─────────────────────────────────────────────────────────────┘
```

SYSTEM AND METHOD FOR DETERMINING RISK OF DIABETES BASED ON BIOCHEMICAL MARKER ANALYSIS

BACKGROUND

Gestational diabetes mellitus (GDM) afflicts approximately 5-12% of pregnancies. Gone untreated, the repercussions of GDM can be severe for both mother and child. Mothers with GDM are more susceptible to pre-eclampsia during pregnancy and developing type 2 diabetes after pregnancy, and children have an increased risk for elevated birth weight, delivery complications, low blood sugar or jaundice at birth, and greater likelihood of developing type 2 diabetes and obesity. If diagnosed early, GDM is amenable to treatment; however, because GDM may outwardly be asymptomatic, it often goes undetected until traditional tests such as blood glucose levels are performed after the second or third trimester of pregnancy has begun. There is a need for tests, systems, and methods for predicting the risk of development of GDM during pregnancy.

SUMMARY

The present disclosure is directed to methods, apparatus, medical profiles and kits useful for determining the risk that a pregnant individual will develop gestational diabetes mellitus (GDM). As is described, this risk can be determined based on the amounts of one or more of the biochemical markers plasminogen activator inhibitor 2 (PAI-2) and soluble tumor necrosis factor receptor 1 (sTNFR1) present in a biological sample taken from the pregnant individual. Additional biochemical markers, biophysical markers, maternal history parameters, maternal demographic parameters, and/or maternal biophysical measurements can also be used when determining the risk of GDM according to methods described herein.

Also described herein are methods, apparatus, medical profiles and kits useful for determining the risk that an individual has or will develop Type 2 diabetes. As is described, this risk can be determined based on the amounts of one or more of the biochemical markers PAI-2 and sTNFR1 present in a biological sample taken from the individual. Additional biochemical markers, biophysical markers, patient history parameters, patient demographic parameters, and/or patient biophysical measurements can also be used when determining the risk of GDM according to methods described herein.

In one aspect, the present disclosure relates to a method for predicting risk of gestational diabetes mellitus (GDM) in a pregnant individual, the method including measuring one or more biochemical markers in a blood sample obtained from the pregnant individual to determine one or more biomarker levels, where the one or more measured biochemical markers includes at least one of PAI-2 and sTNFR1, identifying, by a processor of a computing device, for each of the one or more measured biochemical markers, a difference between the measured biomarker level and a corresponding predetermined control level, and, responsive to the identifying, determining, by the processor, a prediction corresponding to a relative risk of the pregnant individual having or developing GDM.

In some embodiments, the pregnant individual has not been previously diagnosed as diabetic. The difference may include at least one of a threshold value and a percentage difference. The prediction may be based in part upon at least one maternal history factor of the pregnant individual. The at least one maternal history factor may include one of a gestational age, a weight, a BMI, a family history status, a race, and a smoking status.

In some embodiments, the one or more measured biomarkers includes PAI-2, and the identifying step includes identifying, by the processor of the computing device, whether the measured PAI-2 level differs by at least a corresponding threshold amount from a predetermined control PAI-2 level. The one or more measured biomarkers may include PAI-2, and the identifying step may include identifying, by the processor of the computing device, whether a score based at least in part on the measured PAI-2 level is indicative of the risk of the pregnant individual having or developing GDM.

In some embodiments, the one or more measured biomarkers includes sTNFR1, and the identifying step includes identifying, by the processor of the computing device, whether the measured sTNFR1 level differs by at least a corresponding threshold amount from a predetermined control sTNFR1 level. The one or more measured biomarkers may include sTNFR1, and the identifying step may include identifying, by the processor of the computing device, whether a score based at least in part on the measured sTNFR1 level is indicative of the risk of the pregnant individual having or developing GDM.

In some embodiments, the one or more measured biomarkers includes PAI-2 and sTNFR1, and the identifying step includes: identifying, by the processor of the computing device, at least one of (i) to (iii): (i) whether the measured PAI-2 level differs by at least a corresponding threshold amount from a predetermined control PAI-2 level, (ii) whether the measured sTNFR1 level differs by at least a corresponding threshold amount from a predetermined control sTNFR1 level, and (iii) whether a score based on at least the measured PAI-2 level and the sTNFR1 level is indicative of the risk of the pregnant individual having or developing GDM.

In some embodiments, determining the prediction includes calculating a risk assessment score. The risk assessment score may include a proportional risk value. The risk assessment score may include a numeric risk score assigned on a scale.

In some embodiments, a first biomarker of the one or more measured biomarkers is PAI-2, and the prediction is positive based at least in part upon identifying a PAI-2 level reflects a statistically significant decrease in comparison to a respective control level. A first biomarker of the one or more measured biomarkers may be sTNFR1, and the prediction may be positive based at least in part upon identifying an sTNFR1 level reflects a statistically significant increase in comparison to a respective control level.

In some embodiments, the pregnant individual is within a first trimester stage of pregnancy at time of obtaining the blood sample. The first trimester stage may range from forty-two days from conception to ninety-seven days from conception. The blood sample may include one of a plasma sample and a serum sample. Measuring the one or more biochemical markers may include performing an immunoassay. Measuring the one or more biochemical markers may include applying mass spectrometry analysis. Measuring the one or more biochemical markers may include determining a concentration of each respective biochemical marker. Measuring the one or more biochemical markers may include determining a quantity of each respective biochemical marker.

In one aspect, the present disclosure relates to a system for predicting risk of gestational diabetes mellitus (GDM) in a pregnant individual including an in vitro diagnostics kit including testing instruments for testing a blood sample obtained from the pregnant individual for one or more biochemical markers, where the one or more biochemical markers includes at least one of PAI-2 and sTNFR1. The system may include a non-transitory computer-readable medium having instructions stored thereon, where the instructions, when executed by a processor, cause the processor to retrieve one or more biomarker levels, where each biomarker level of the one or more biomarker levels corresponds to a biochemical marker tested for using the in vitro diagnostics kit, and where the retrieved one or more biomarker levels includes a biomarker level for at least one of PAI-2 and sTNFR1. The instructions, when executed, may cause the processor to calculate a risk assessment score corresponding to a relative risk of the pregnant individual having or developing GDM, where the risk assessment score is based in part upon a comparison of the biomarker level and a corresponding predetermined control level.

In some embodiments, the instructions cause the processor to, prior to calculating the risk assessment score, access at least one maternal history factor of the pregnant individual. Accessing the at least one maternal history factor of the pregnant individual may include causing presentation of a graphical user interface at a display device, where the graphical user interface includes one or more input fields for submitting maternal history factor information regarding the pregnant individual. Accessing the at least one maternal history factor of the pregnant individual may include importing, from an electronic medical record, the at least one maternal history factor.

In some embodiments, the instructions cause the processor to, after calculating the risk assessment score, cause presentation of the risk assessment score at a display device. Causing presentation of the risk assessment score may include causing presentation of risk assessment information. The testing instruments may include at least one of an anti-PAI-2 antibody and an anti-sTNFR1 antibody. The testing instruments may include one or more of an assay buffer, a coated plate, a tracer, and calibrators.

In one aspect, the present disclosure relates to a method for predicting risk of gestational diabetes mellitus (GDM) in a pregnant individual, the method including measuring one or more biochemical markers in a blood sample obtained from the pregnant individual to determine one or more biomarker levels, where the one or more measured biochemical markers includes at least one of PAI-2 and sTNFR1, and calculating, by the processor, a risk assessment score corresponding to a relative risk of the pregnant individual having or developing GDM, where the risk assessment score is based in part upon a comparison of the biomarker level and a corresponding predetermined control level.

In some embodiments, measuring the one or more biochemical markers includes applying mass spectrometry analysis. Measuring the one or more biochemical markers may include performing an immunoassay. Calculating the risk assessment score may include normalizing the comparison of the biomarker level and the corresponding predetermined control level based upon one or more maternal demographic values. Normalizing the comparison may include applying a multiple of mean statistical analysis. Calculating the risk assessment score may include normalizing the comparison of the biomarker level and the corresponding predetermined control level based upon one or more maternal biophysical attributes.

In one aspect, the present disclosure relates to a non-transitory computer readable medium having instructions stored thereon, where the instructions, when executed by a processor, cause the processor to access measurements of one or more biochemical markers, where the measurements were obtained by testing biochemical marker levels in a blood sample obtained from a pregnant individual, and the one or more measured biochemical markers includes at least one of PAI-2 and sTNFR1, and calculate a risk assessment score corresponding to a relative risk of the pregnant individual having or developing gestational diabetes mellitus (GDM), where the risk assessment score is based in part upon a comparison of the biomarker level and a corresponding predetermined control level.

In one aspect, the present disclosure relates to a system for predicting risk of gestational diabetes mellitus (GDM) in a pregnant individual including an in vitro diagnostics kit including testing instruments for testing a blood sample obtained from the pregnant individual for one or more biochemical markers, where the one or more biochemical markers includes at least one of PAI-2 and sTNFR1, and a non-transitory computer-readable medium having instructions stored thereon, where the instructions, when executed by a processor, cause the processor to retrieve one or more biomarker levels, where each biomarker level of the one or more biomarker levels corresponds to a biochemical marker tested for using the in vitro diagnostics kit, and where the retrieved one or more biomarker levels includes a biomarker level for at least one of PAI-2 and sTNFR1, and identify, for each of the one or more measured biochemical markers, a difference between the measured biomarker level and a corresponding predetermined control level, and responsive to the identifying, determine a prediction corresponding to a relative risk of the pregnant individual having or developing GDM.

In one aspect, the present disclosure relates to a non-transitory computer readable medium having instructions stored thereon, where the instructions, when executed by a processor, cause the processor to access measurements of one or more biochemical markers, where the measurements were obtained by testing biochemical marker levels in a blood sample obtained from a pregnant individual, and the one or more measured biochemical markers includes at least one of PAI-2 and sTNFR1, identify, for each of the one or more measured biochemical markers, a difference between the measured biomarker level and a corresponding predetermined control level, and responsive to the identifying, determine a prediction corresponding to a relative risk of the pregnant individual having or developing GDM.

In one aspect, the present disclosure relates to a method for predicting risk of Type 2 diabetes in an individual, the method including measuring one or more biochemical markers in a blood sample obtained from the individual to determine one or more biomarker levels, where the one or more measured biochemical markers includes at least one of PAI-2 and sTNFR1, and calculating, by a processor of a computing device, a risk assessment score corresponding to a relative risk of the individual having or developing Type 2 diabetes, where the risk assessment score is based in part upon a comparison of the biomarker level and a corresponding predetermined control level.

In one aspect, the present disclosure relates to a method for predicting risk of Type 2 diabetes in an individual, the method including measuring one or more biochemical markers in a blood sample obtained from the individual to determine one or more biomarker levels, where the one or more measured biochemical markers includes at least one of PAI-2 and sTNFR1, identifying, by a processor of a computing device, for each of the one or more measured biochemical markers, a difference between the measured biomarker level and a corresponding predetermined control level, and responsive to the identifying, determining, by the processor, a prediction corresponding to a relative risk of the individual having or developing Type 2 diabetes.

BRIEF DESCRIPTION OF THE FIGURES

The foregoing and other objects, aspects, features, and advantages of the present disclosure will become more apparent and better understood by referring to the following description taken in conjunction with the accompanying drawings, in which:

FIGS. 4A through 4D are Receiver Operation Characteristic (ROC) curves demonstrating various combinations of the PAI-2 biochemical marker, the sTNFR1 biochemical marker, and demographic-based evaluation of one or both of the PAI-2 and sTNFR1 biochemical markers in the prediction of gestational diabetes mellitus;

FIG. 5 is a flow chart of an example method for determining a prediction corresponding to a relative risk of a pregnant individual having or developing gestational diabetes mellitus.

Figure 1:
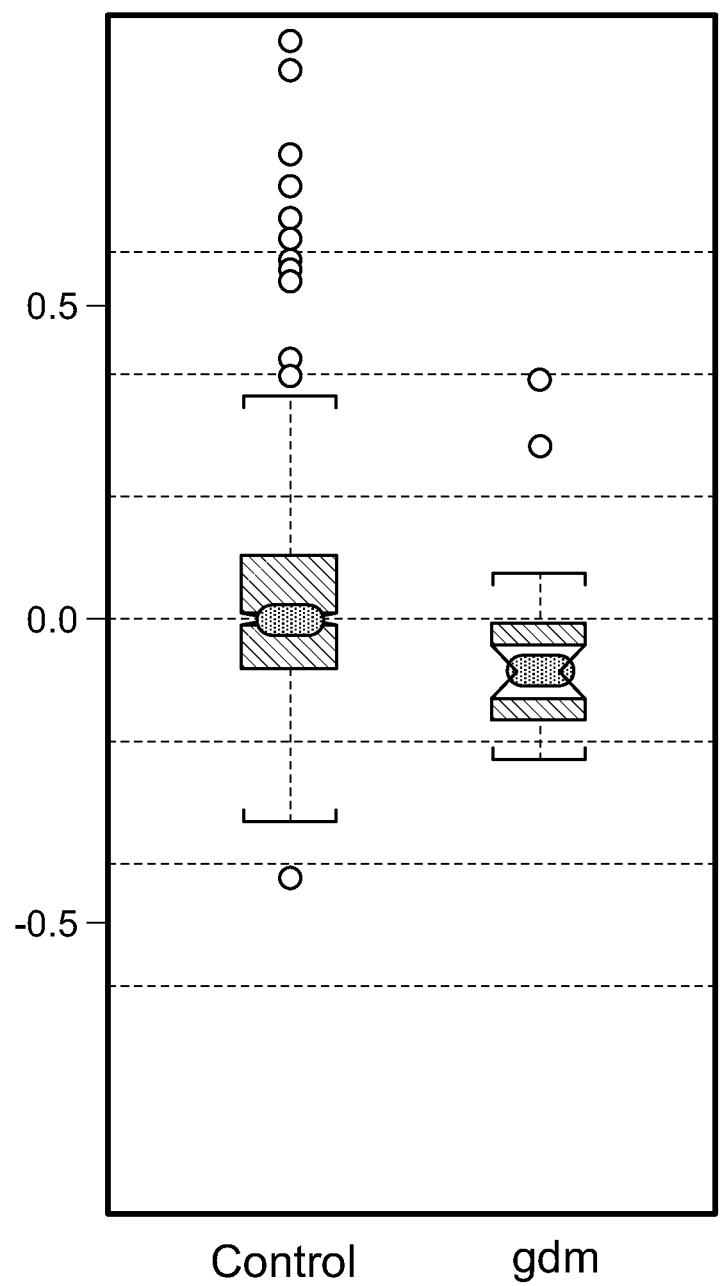
FIG. 1 is a box-whisker plot of PAI-2 multiple of the median (MoM) in two pregnancy outcome groups: control and gestational diabetes mellitus.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

In some implementations, the present disclosure may be directed to methods, apparatus, medical profiles and kits useful for determining the risk that a pregnant individual will develop gestational diabetes mellitus (GDM). As is described, this risk can be determined based on the amounts of one or more of the biochemical markers plasminogen activator inhibitor 2 (PAI-2) and soluble tumor necrosis factor receptor 1 (sTNFR1) present in a biological sample taken from the pregnant individual. Additional biochemical markers, biophysical markers, maternal history parameters, maternal demographic parameters, and/or maternal biophysical measurements can also be used when determining the risk of GDM according to methods described herein.

Also described herein are methods, apparatus, medical profiles and kits useful for determining the risk that an individual has or will develop Type 2 diabetes. As is described, this risk can be determined based on the amounts of one or more of the biochemical markers PAI-2 and sTNFR1 present in a biological sample taken from the individual. Additional biochemical markers, biophysical markers, patient history parameters, patient demographic parameters, and/or patient biophysical measurements can also be used when determining the risk of GDM according to methods described herein.

As is described in Examples 1 and 2, statistical analysis of a clinical population was performed, revealing each of biochemical markers PAI-2 and sTNFR1 were remarkably effective for determining risk of GDM with clinically acceptable detection and false positive rates. As used herein the "% detection" is the percentage-expressed proportion of affected (for example, GDM-positive) individuals with a positive result. The "% false positive" is the percentage-expressed proportion of unaffected individuals with a positive result. The predictive power of a marker or combination thereof is commonly expressed in terms of the detection rate for a given false positive rate.

To improve risk evaluation, in some implementations, a number of risk-related factors may be considered in combination with the evaluation of biochemical marker levels of an individual. For example, an algorithm for predicting risk of having or developing GDM may involve one or more of additional biochemical markers, patient history parameters, patient demographic parameters, and/or patient biophysical measurements. Patient history parameters, in some examples, can include parity, smoking history, past medical conditions, and family history of gestational and/or Type 2 diabetes. Patient demographic parameters, in some examples, can include age, ethnicity, current medications, and vegetarianism. Patient biophysical measurements, in some examples, may include weight, body mass index (BMI), blood pressure, heart rate, cholesterol levels, triglyceride levels, medical conditions (e.g., metabolic syndrome, insulin resistance, atherosclerosis, kidney disease, heart disease, acanthosis nigricans, polycystic ovary syndrome), and gestational age.

The selection of one or both of the biochemical markers PAI-2 and sTNFR1 to be used in a clinical or other laboratory settings can depend on a variety of practical considerations, including the available medical equipment and biochemical marker testing reagents in the particular setting.

As used herein, the term "gestational diabetes mellitus" refers to a condition in a pregnant individual characterized by glucose intolerance and/or reduced activity of insulin.

In instances where a pregnant individual is determined to have an increased risk of developing GDM using a method as described herein, the individual can receive therapy or lifestyle advice from a health care provider. For example, a health care provider may prescribe medication including one or more of a meglitinide (e.g., repaglinide, nateglinide), a sulfonylurea (e.g., glipizide, glimepiride, glyburide) a dipeptidy peptidase-4 inhibitor (e.g., saxagliptin, sitagliptin, linagliptin), a biguanide (e.g., metformin), a thiazolidinedione (e.g., rosiglitazone, pioglitazone), an alpha-glucosidase inhibitor (e.g., acarbose, miglitol), an islet amyloid polypeptide mimetic (e.g., pramlintide), an incretin mimetic (e.g., exenatide, liraglutide), and an insulin. Additionally, or alternatively, a health care provider may recommend a change in diet or increased level of exercise.

Examples 1 and 2 describe that risk of GDM can be determined using particular biochemical markers, using blood samples that were collected within the first trimester of pregnancy (e.g., up to 14 weeks of gestation). Thus, for use in the methods for detecting GDM, a sample can be collected between about 9 and 37 weeks gestation, inclusive, including between about 9 and 14 weeks, inclusive, and more generally, prior to about 14 weeks, within first trimester after about 9 weeks, within second trimester and within third trimester. Although earlier testing is often a beneficial policy from a public health perspective, it is understood that collection of samples can sometimes be affected by practical considerations such as a woman delaying a visit to her health care provider until relatively later weeks of gestation.

In certain circumstances, biological samples can be collected on more than one occasion from a pregnant individual, for example, when her risk assessment score requires monitoring for development of GDM due to a priori risk, presentation of symptoms and/or other factors. The methods for determining risk of GDM described herein can also be used for monitoring a pregnant individual who is undergoing a therapy or treatment for a pre-diabetic condition. If desired, testing of biochemical markers can be carried out in a home setting, such as by using dipstick biochemical test formats for home use and a personal computing device for interpreting the results-.

The methods for determining the risk of GDM in a pregnant individual involve determining the amount of one or more biochemical markers selected from PAI-2 and sTNFR1.

The methods for determining the risk of GDM in a pregnant individual involve using a biological sample from the pregnant individual. The biological sample can be any body fluid or tissue sample that contains the selected biochemical markers. Examples 1 and 2 describe use of maternal blood in the form of plasma. The choice of biological sample can often depend on the assay formats available in a particular clinical laboratory for testing amounts of markers. For example, some assay formats lack sensitivity needed for assaying whole blood, such that a clinical laboratory opts for testing a fraction of blood, such as serum, or using dried blood. Exemplary biological samples useful for the methods described herein include blood, purified blood products (such as serum, plasma, etc.), urine, amniotic fluid, a chorionic villus biopsy, a placental biopsy and cervicovaginal fluid. Amounts of biochemical markers present in a biological sample can be determined using any assay format suitable for measuring proteins in biological samples. A common assay format for this purpose is the immunoassay, including, for example, enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); dissociation-enhanced lanthanide fluorescent immunoassay (DELFIA) and chemiluminescence assays (CL). Amounts of biochemical markers present in a biological sample may also be measured by mass spectrometry, for example, by relative or absolute quantitative mass spectrometry using labeled or unlabeled proteins.

To determine whether the amount of biochemical markers is greater than or less than normal, the normal amount of biochemical marker present in a maternal biological sample from a relevant population is determined. The relevant population can be defined based on any characteristics than can affect normal (unaffected) amounts of the markers. For determining risk of GDM, the relevant population can be established on the basis of low risk for GDM. Once the normal marker amounts are known, the determined marker amounts can be compared and the significance of the difference determined using standard statistical methods. When there is a statistically significant difference between the determined marker amount and the normal amount, there is a significant risk that the tested individual will develop GDM.

The risk that a pregnant individual develops GDM can be determined from biochemical marker amounts using statistical analysis based on clinical data collected in a patient population study. Examples 1 and 2 show results from such studies. There are multiple statistical methods for combining parameters that characterize the pregnant individual, such as amounts of biochemical markers, to obtain a risk estimate. The likelihood method (Palomaki and Haddow, 1987) and the linear discriminant function method (Norgarrd-Pedersen et al. Clin. Genet. 37, 35-43 (1990)) are commonly used for this purpose. The basic principle of the likelihood method is that the population distributions for a parameter (such as the amount of a biochemical marker) are known for the 'unaffected' and 'affected' groups. Thus, for any given parameter (such as amount of marker), the likelihood of membership of the 'unaffected' and 'affected' groups can be calculated. The likelihood is calculated as the Gaussian height for the parameter based on the population mean and standard deviation. The 'likelihood ratio' is the ratio of the heights calculated using 'unaffected' and 'affected' population parameters, and is an expression of the increased risk of having a disorder, with respect to a prior risk.

An overview for determining risk in accordance with the methods described herein follows. In current chromosomal abnormality screening practice, biochemical marker values are being referred to smoothed median values to produce adjusted multiple of the median (MoM) values to standardize for factors such as assay, gestation, maternal weight, smoking status, and the like. This is done, for example, because the amounts of biochemical markers in the individual's body change with gestation, in order to calculate risks, the biochemical marker value is adjusted to be unaffected by gestational age. The value of a MoM for a sample is the ratio of the biochemical marker value to the population median value at the same gestational age (or other parameter). The Gaussian heights for biochemical marker results are determined for the 'unaffected' and 'affected' population parameters. The ratio of the height on the 'unaffected' curve and the height on the 'affected' curve is determined. The prior odds are multiplied by this ratio.

Conceptually, calculating risk using two or more biochemical markers requires first that individual likelihood ratios be defined for each of the markers (first corrected for one or more factors such as one or more biophysical markers, maternal history parameters, maternal demographic parameters, and/or maternal biophysical measurements) and then combined (e.g., multiplied) together. In some implementations, an additional factor is introduced in the calculation to account for the extent of overlap of information (correlation) of the two or more individual biochemical markers. For example, r-values may be used to express the correlation between parameters, such as our example of two individual biochemical markers.

Figure 2:
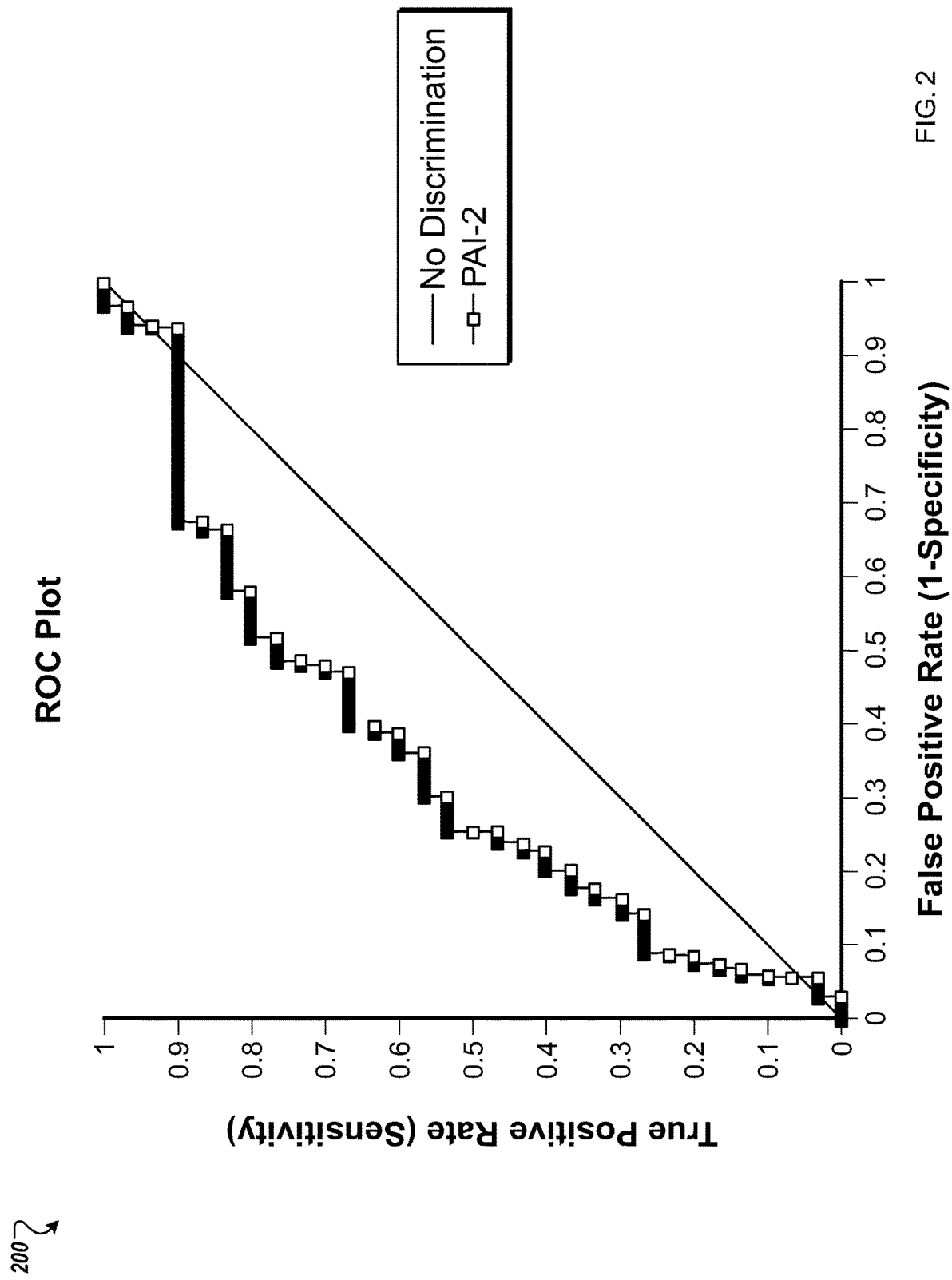
FIG. 2 is a Receiver Operation Characteristic (ROC) curve for the prediction of gestational diabetes mellitus using the PAI-2 biochemical marker.
Figure 3:
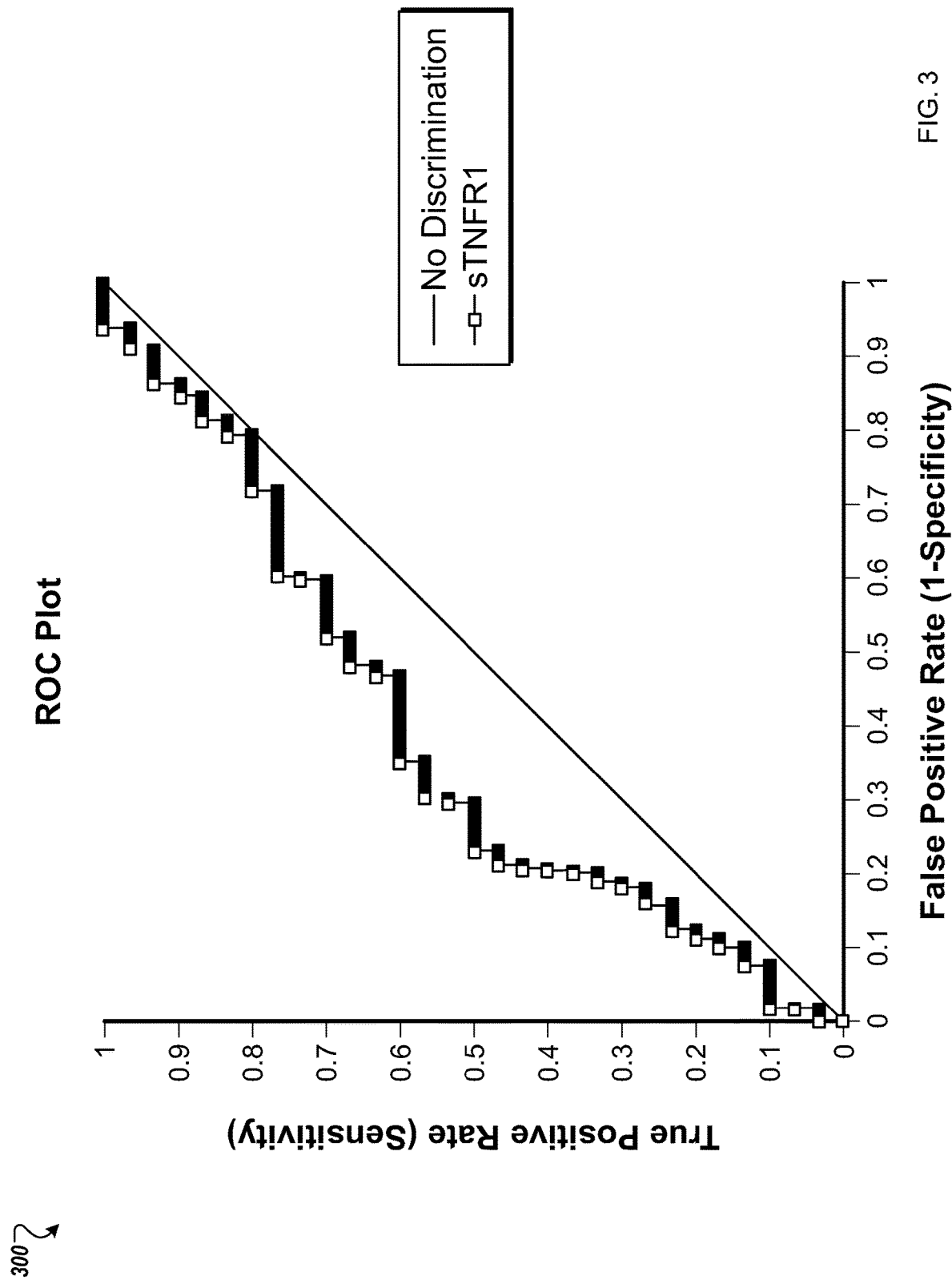
FIG. 3 is a Receiver Operation Characteristic (ROC) curve for the prediction of gestational diabetes mellitus using the sTNFR1 biochemical marker.

Turning to FIGS. 4A through 4D, a series of Receiver Operation Characteristic (ROC) curves demonstrate synergistic benefits that may be obtained, in comparison, for example, to the outcomes plotted in relation to the ROC curve 200 of FIG. 2 and the ROC curve 300 of FIG. 3, through the use of various combinations of the PAI-2 biochemical marker, the sTNFR1 biochemical marker, and demographic-based evaluation of one or both of the PAI-2 and sTNFR1 biochemical markers in the prediction of gestational diabetes mellitus. As illustrated in Table 1, below, the area under the ROC curve 200 (e.g., PAI-2 alone) is 0.65, and the area under the ROC curve 300 (e.g., sTNFR1) is 0.62. An area under the curve for a ROC curve (not illustrated) of demographics alone (e.g., gestational age, patient weight, and cigarette smoking status) is 0.78.

Figure 4A:
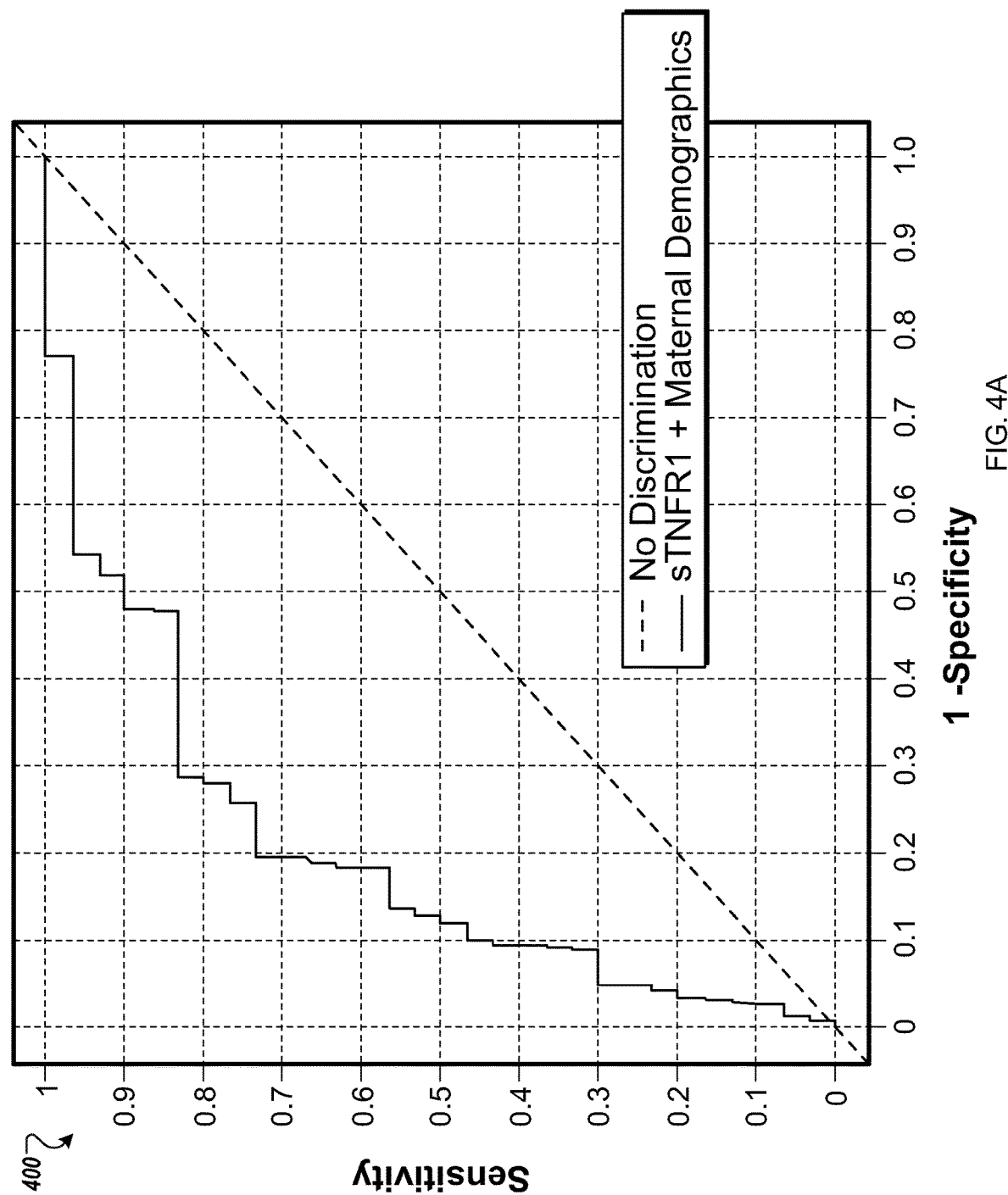
Figure 4C:
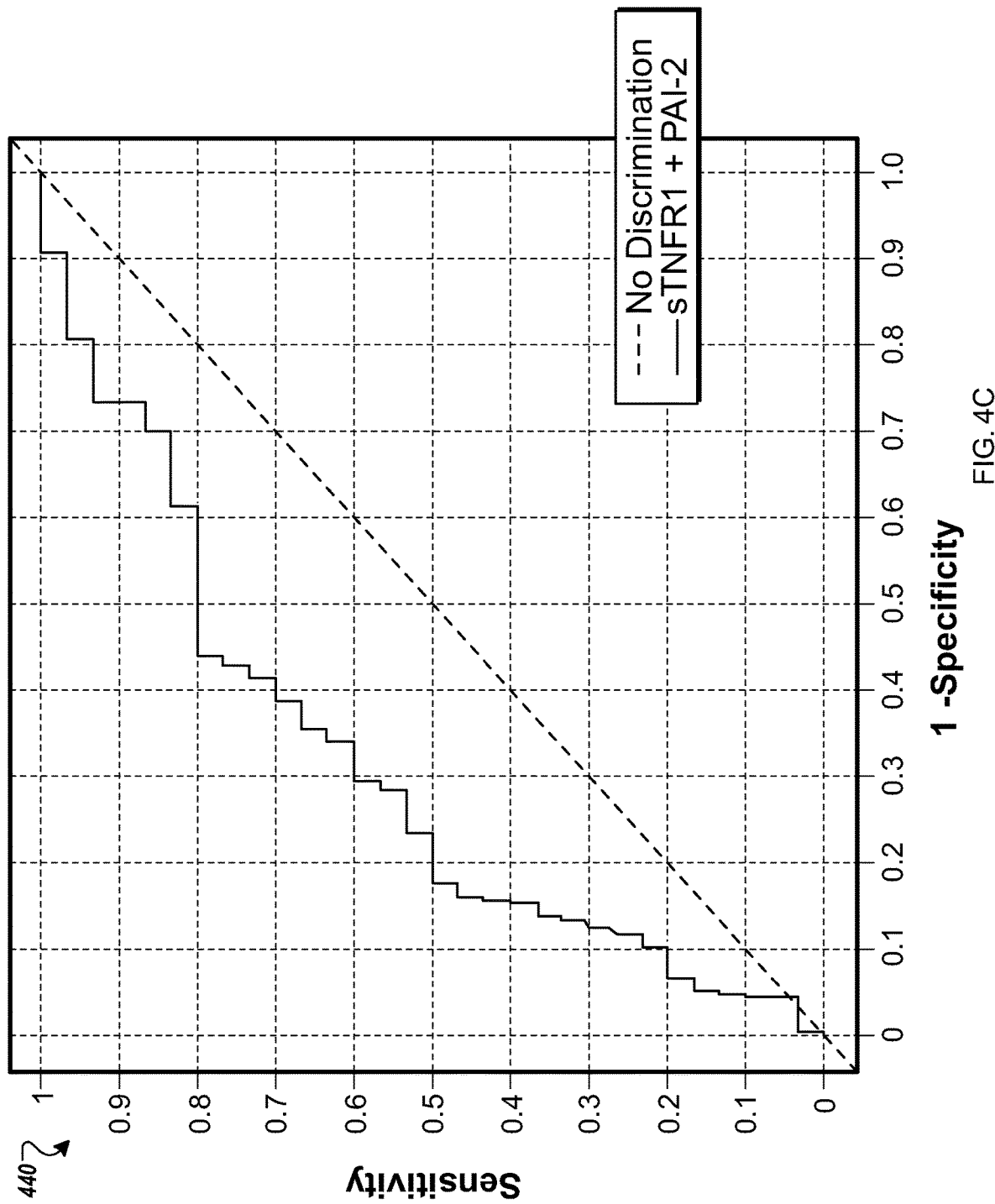
Figure 4D:
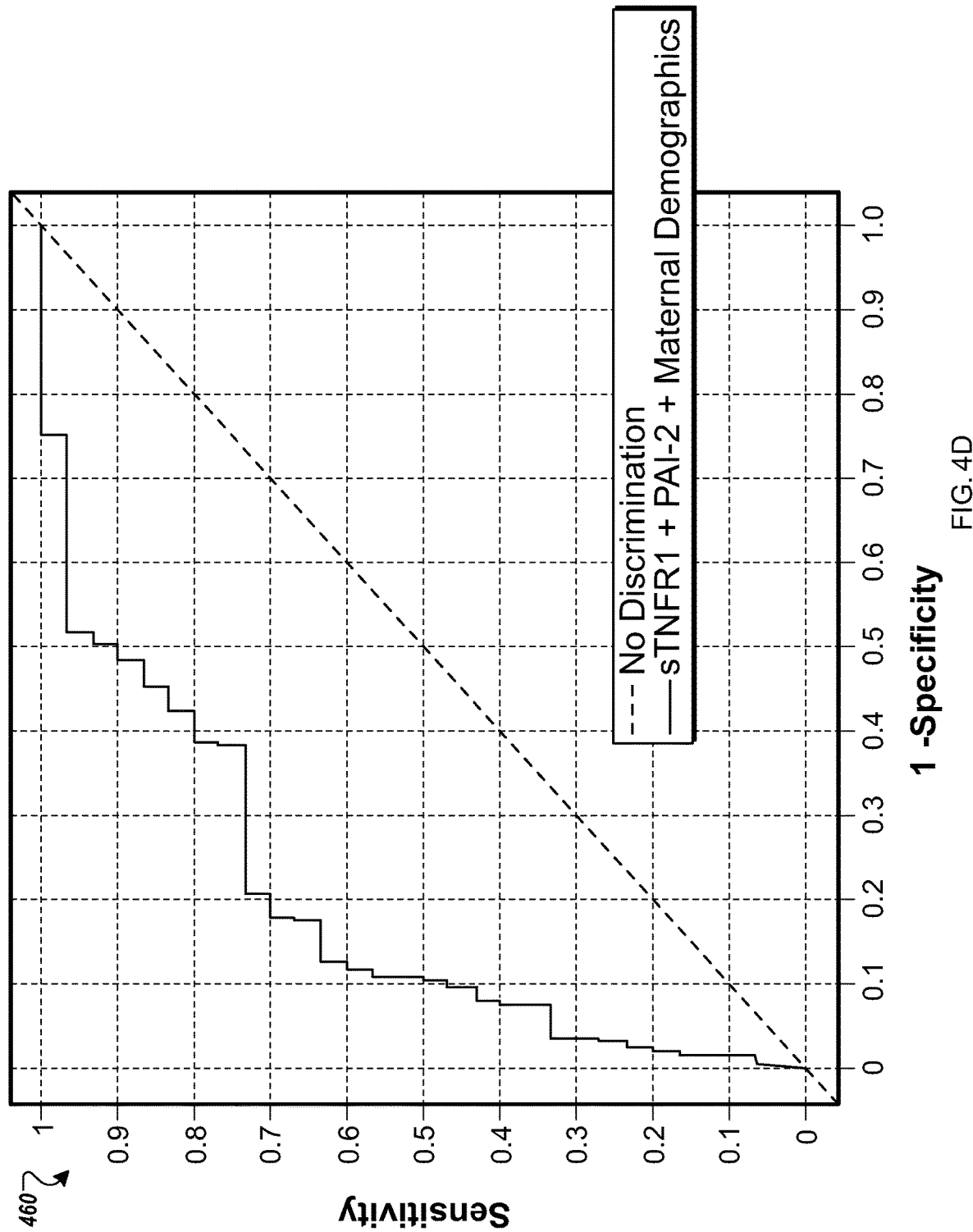

In comparison, turning to FIG. 4A, a ROC curve 400 demonstrates performance of the combination of analysis of a sTNFR1 biochemical marker plus statistical analysis of maternal demographic information including gestational age, patient weight, and cigarette smoking status (e.g., yes or no). The area under the ROC curve 400 is 0.81. Turning to FIG. 4B, a ROC curve 420 demonstrates performance of the combination of analysis of a PAI-2 biochemical marker plus statistical analysis of maternal demographic information including gestational age, patient weight, and cigarette smoking status (e.g., yes or no). The area under the ROC curve 420 is 0.78. Turning to FIG. 4C, a ROC curve 440 demonstrates performance of the combination of analysis of both a sTNFR1 biochemical marker and a PAI-2 biochemical marker. The area under the curve of ROC curve 440 is 0.69. Finally, turning to FIG. 4D, a ROC curve 460 demonstrates performance of the combination of analysis of both a sTNFR1 biochemical marker and a PAI-2 biochemical marker plus statistical analysis of maternal demographic information including gestational age, patient weight, and cigarette smoking status (e.g., yes or no). The area under the curve of ROC curve 460 is 0.81.

| Test | Area |
|---|---|
| PAI-2 | 0.65 |
| sTNFR1 | 0.62 |
| Demographics | 0.78 |
| sTNFR1 + Demographics | 0.81 |
| PAI-2 + Demographics | 0.78 |
| sTNFR1 + PAI-2 | 0.69 |
| sTNFR1 + PAI-2 + Demographics | 0.81 |

As is described in Example 1, statistical analyses of clinical data, including amounts of biochemical marker PAI-2, were carried out to determine the risk of a pregnant individual developing GDM. According to Example 1, for the biochemical marker PAI-2, a MoM is calculated. The MoM was then adjusted based on parameters including gestational age, patient weight, and cigarette smoking status of each sample.

Turning to FIG. 5, a flow chart illustrates an example method 500 for using biomarker level measurements in determining a risk prediction for GDM in a pregnant individual. The method 500, for example, may be provided as a software algorithm for use with GDM biochemical marker testing (e.g., packaged and/or bundled with a GDM diagnostic test kit).

In some implementations, the method 500 begins with obtaining measurements, from a biological sample, of one or more biomarker levels corresponding to one or more biochemical markers (502). The biochemical markers include at least one of PAI-2 and sTNFR1. The measurements may be obtained in relation to the methods described above for measuring levels of one or both of the PAI-2 and sTNFR1 in a blood sample, such as a plasma sample or a serum sample. The blood sample, for example, may be collected during a first trimester of pregnancy. In some implementations, a clinician or other medical professional enters the measurements into a graphical user interface dialogue of a software application for identifying a risk of a pregnant individual having or developing GDM. The graphical user interface dialogue, for example, may include one or more drop-down menus, data entry boxes, radio buttons, check boxes, and the like for entering measurements related to the one or more biomarker levels as well as, in some embodiments, information regarding the pregnant individual.

In some implementations, for each of the one or more biomarker levels, a difference between the biomarker level and a corresponding predetermined control level is identified (504). The difference, in some examples, can include a threshold difference or a percentage difference between the measurement value and the control value. The predetermined control level, in some implementations, depends at least in part upon profile data obtained in relation to the pregnant individual, such as one or more demographic values and/or one or more biophysical values. In a particular example, the predetermined control level is identified based at least in part upon one or more of an age, a weight (BMI), an ethnicity, and a cigarette smoking status of the pregnant individual. The predetermined control level, in another example, is identified based at least in part upon a gestational age of the pregnant individual's fetus.

In some implementations, one or more demographic values associated with the pregnant individual are accessed (506). In some examples, the demographic values can include one or more of age, ethnicity, current medications, and vegetarianism. The demographic values, in some implementations, may additionally include patient history parameters such as, in some examples, smoking history, past medical conditions, and family history of gestational and/or Type 2 diabetes. The demographic values, in some implementations, are accessed via a dialogue interface. For example, a graphical user interface may be presented to a doctor or clinician for entering one or more demographic values related to the pregnant individual. In some implementations, the demographic values are accessed via a medical record system. For example, the demographic values may be imported into the software from a separate (e.g., medical facility) computing system.

In some implementations, one or more biophysical values associated with the pregnant individual are accessed (508). Patient biophysical measurements, in some examples, may include weight, body mass index (BMI), medical conditions, and gestational age. The patient biophysical values, in some implementations, are accessed via a dialogue interface. For example, a graphical user interface may be presented to a doctor or clinician for entering one or more biophysical values related to the pregnant individual. In some implementations, the patient biophysical values are accessed via a medical record system. For example, the patient biophysical values may be imported into the software from a separate (e.g., medical facility) computing system.

In some implementations, a risk assessment score corresponding to a relative risk of the pregnant individual having or developing GDM is determined (510). The risk assessment score is based in part upon the biomarker level(s) (e.g., the actual levels and/or a difference between the levels and predetermined control levels). In some implementations, the risk assessment score is based in part upon additional factors, such as the demographic values and/or the biophysical values. The risk assessment score, in some implementations, includes a numeric value corresponding to a proportional risk of the pregnant individual having or developing GDM. In some implementations, the risk assessment score includes a ranking on a scale (e.g., 1 to 10, 1 to 100, etc.) of a relative risk of the pregnant individual having or developing GDM. The risk assessment score, in some implementations, includes a percentage likelihood of the pregnant individual having or developing GDM.

In some implementations, the risk assessment score is presented upon the display of a user computing device (512).

The risk assessment score, in some implementations, is presented on a display of a computing device executing the software application for determining risk of GDM in a pregnant individual. In some implementations, the risk assessment score is presented as a read-out on a display portion of a specialty computing device (e.g., a test kit analysis device). The risk assessment score may be presented as a numeric value, bar graph, pie graph, or other illustration expressing a relative risk of the pregnant individual having or developing GDM.

Although described in relation to a pregnant individual, the method 500 may be used to identify a risk associated with an individual having or developing Type 2 diabetes. In some implementations, more or fewer steps are included in the method 500, or one or more of the steps of the method 500 may be performed in a different order. For example, in some implementations, demographic values (506) and/or biophysical values (508) are not accessed. In some implementations, rather than identifying a difference between the biomarker level and a corresponding predetermined control level (504), the biomarker level(s) obtained in step 502 are combined with one or both of demographic value(s) and biophysical value(s) to determine a risk assessment score (510). In other implementations, a difference between the biomarker level and the corresponding predetermined control level (504) is used to determine a prediction (not illustrated) of risk of having or developing GDM, without generating a risk score in relation to the additional profile values listed in steps 506 and 508. Rather than presenting the risk assessment score on a display of a computing device, in some implementations, a graphic (e.g., "+" for positive, "−" for negative, etc.), a color coding (e.g., red for positive, yellow for indeterminate, green for negative, etc.), or a verbal indication (e.g., as issued via a speaker device in communication with a processor) may be provided as outcome of the analysis. Other modifications of the method 500 are possible.

It is understood that the number values can be different for different study populations, although those shown below provide an acceptable starting point for risk calculations. For example, it has been observed that for a particular clinical center carrying out patient risk analysis, the number values in a risk algorithm can drift over time, as the population in the served region varies over time.

The present disclosure also provides commercial packages, or kits, for determining the risk that a pregnant individual will develop GDM. Such kits can include one or more reagents for detecting the amount of at least one biochemical marker in a biological sample from a pregnant individual, wherein the at least one biochemical markers are selected from PAI-2 and sTNFR1 as well as, in some implementations, one or more of a coated plate, a tracer, calibrators, instructions for carrying out the test, and software for analyzing biomarker level measurement results in relation to a particular pregnant individual.

Example 1: Case-Control Study Using Plasminogen Activator Inhibitor 2 (PAI-2) Biochemical Marker for Determining Risk of Gestational Diabetes Mellitus in a Pregnant Individual This example shows use of the PAI-2 biochemical marker for determining risk of GDM in a pregnant individual.

A retrospective case-control study was undertaken using leftover first trimester maternal plasma samples. The dataset included 449 control samples and 30 cases of GDM outcome. The PAI-2 biochemical marker was measured from these samples using a sandwich immunoassay kit.

For the analyses described herein, the measurement results were converted to multiples of median (MoM) by taking into account the gestational age, maternal weight, and cigarette smoking status of the pregnant individual associated with each plasma sample.

As illustrated in FIG. 1, a box-whisker plot 100 of PAI-2 multiple of the median (MoM) in a control pregnancy outcome group and a gestational diabetes mellitus pregnancy outcome group illustrates that the amount of PAI-2 in biological samples from pregnant individuals is lower when the individual has a GDM outcome in pregnancy. The case study identified a decrease in PAI-2 level of the GDM outcome population of approximately −0.59 (multiples of control population standard deviations in $\log_{10}$ MoMs) in relation to the control population. A Wilcoxon rank-sum test done with the results of the study showed that PAI-2 had a statistically significant difference in the results of the cases as compared to the controls (p=0.01). A Mahalanobis distance between the control pregnancy outcome group and the gestational diabetes mellitus pregnancy outcome group was calculated as 0.7.

Receiver Operation Characteristic (ROC) analysis of the results of the case study, illustrated in relation to a curve 200 of FIG. 2, demonstrates performance of prediction of gestational diabetes mellitus using the PAI-2 biochemical marker. Table 2 illustrates data obtained from the curve 200. As presented below in relation to Table 2, the area under the ROC curve was 0.65 (Confidence Interval (CI) of 95%, p=0.0017).

| Test | Area | 95% CI | SE | Z | p | ROC from plasma data GDM = GDM on insulin |
|---|---|---|---|---|---|---|
| PAI-2 | 0.65 | 0.55 to 0.76 | 0.053 | 2.94 | 0.0017 | Have lower values |

Thus, this example shows that in screening for GDM, there was significant independent contributions from maternal blood PAI-2. Screening by PAI-2 alone, for example, was estimated to identify about 35% of individuals developing GDM at a false positive rate of about 20%. In another example, screening by PAI-2 was estimated to identify about 55% of individuals developing GDM at a false positive rate of about 30%.

Example 2: Case-Control Study Using Soluble TNF Receptor 1 (sTNFR1) Biochemical Marker for Determining Risk of Gestational Diabetes Mellitus in a Pregnant Individual This example shows use of the sTNFR1 biochemical marker for determining risk of GDM in a pregnant individual.

A second retrospective case-control study was undertaken using the leftover first trimester maternal plasma samples as described in relation to the case-control study of Example 1, above. The sTNFR1 biochemical marker was measured from these samples using a sandwich immunoassay kit.

For the analyses described herein, the measurement results were converted to multiples of median (MoM) by taking into account the gestational age, maternal weight, and cigarette smoking status of the pregnant individual associated with each plasma sample.

Calculation of sTNFR1 multiple of the median (MoM) in a control pregnancy outcome group and a gestational diabetes mellitus pregnancy outcome group determined that the amount of sTNFR1 in biological samples from pregnant individuals is higher when the individual has a GDM outcome in pregnancy. The case study identified an increase in sTNFR1 level of the GDM outcome population of approximately 0.58 (multiples of control population standard deviations in $\log_{10}$ MoMs) in relation to the control population. A Wilcoxon rank-sum test done with the results of the study showed that sTNFR1 had a statistically significant difference in the results of the cases as compared to the controls. A Mahalanobis distance between the control pregnancy outcome group and the gestational diabetes mellitus pregnancy outcome group was calculated as 0.57.

Receiver Operation Characteristic (ROC) analysis of the results of the case study, illustrated in relation to a curve 300 of FIG. 3, demonstrates performance of prediction of gestational diabetes mellitus using the sTNFR1 biochemical marker. Table 3 illustrates data obtained from the curve 300. As presented below in relation to Table 3, the area under the ROC curve was 0.61 (Confidence Interval (CI) of 95%, p=0.0213).

| Test | Area | 95% CI | SE | Z | p | ROC from plasma data GDM = GDM on insulin |
|---|---|---|---|---|---|---|
| sTNFR1 | 0.61 | 0.50 to 0.73 | 0.057 | 2.03 | 0.00213 | Have higher values |

Thus, this example shows that in screening for GDM, there was significant independent contributions from maternal blood sTNFR1. Screening by sTNFR1 alone, for example, was estimated to identify about 35% of individuals developing GDM at a false positive rate of about 20%. In another example, screening by sTNFR1 was estimated to identify about 50% of individuals developing GDM at a false positive rate of about 30%.

Figure 6:
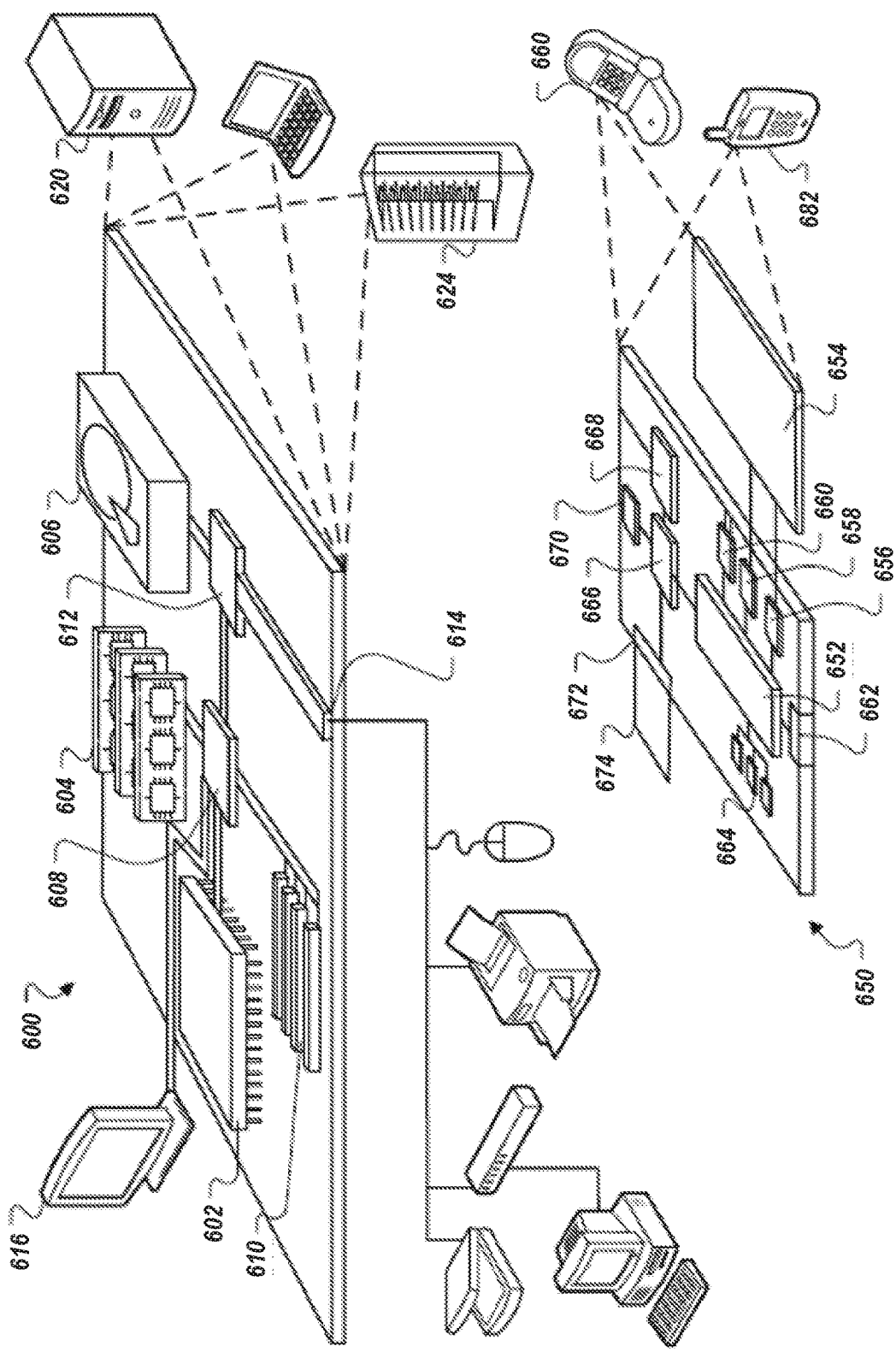
FIG. 6 is a block diagram of a computing device and a mobile computing device.

FIG. 6 shows an example of a computing device 600 and a mobile computing device 650 that can be used to implement the techniques described in this disclosure. The computing device 600 is intended to represent various forms of digital computers, such as laptops, desktops, workstations, personal digital assistants, servers, blade servers, mainframes, and other appropriate computers. The mobile computing device 650 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 600 includes a processor 602, a memory 604, a storage device 606, a high-speed interface 608 connecting to the memory 604 and multiple high-speed expansion ports 610, and a low-speed interface 612 connecting to a low-speed expansion port 614 and the storage device 606. Each of the processor 602, the memory 604, the storage device 606, the high-speed interface 608, the high-speed expansion ports 610, and the low-speed interface 612, are interconnected using various busses, and may be mounted on a common motherboard or in other manners as appropriate. The processor 602 can process instructions for execution within the computing device 600, including instructions stored in the memory 604 or on the storage device 606 to display graphical information for a GUI on an external input/output device, such as a display 616 coupled to the high-speed interface 608. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 604 stores information within the computing device 600. In some implementations, the memory 604 is a volatile memory unit or units. In some implementations, the memory 604 is a non-volatile memory unit or units. The memory 604 may also be another form of computer-readable medium, such as a magnetic or optical disk.

The storage device 606 is capable of providing mass storage for the computing device 600. In some implementations, the storage device 606 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 602), perform one or more methods, such as those described above. The instructions can also be stored by one or more storage devices such as computer- or machine-readable mediums (for example, the memory 604, the storage device 606, or memory on the processor 602).

The high-speed interface 608 manages bandwidth-intensive operations for the computing device 600, while the low-speed interface 612 manages lower bandwidth-intensive operations. Such allocation of functions is an example only. In some implementations, the high-speed interface 608 is coupled to the memory 604, the display 616 (e.g., through a graphics processor or accelerator), and to the high-speed expansion ports 610, which may accept various expansion cards (not shown). In the implementation, the low-speed interface 612 is coupled to the storage device 606 and the low-speed expansion port 614. The low-speed expansion port 614, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 600 may be implemented in a number of different forms, as shown in the figure. For example, it may be implemented as a standard server 620, or multiple times in a group of such servers. In addition, it may be implemented in a personal computer such as a laptop computer 622. It may also be implemented as part of a rack server system 624. Alternatively, components from the computing device 600 may be combined with other components in a mobile device (not shown), such as a mobile computing device 650. Each of such devices may contain one or more of the computing device 600 and the mobile computing device 650, and an entire system may be made up of multiple computing devices communicating with each other.

The mobile computing device 650 includes a processor 652, a memory 664, an input/output device such as a display 654, a communication interface 666, and a transceiver 668, among other components. The mobile computing device 650 may also be provided with a storage device, such as a micro-drive or other device, to provide additional storage. Each of the processor 652, the memory 664, the display 654, the communication interface 666, and the transceiver 668, are interconnected using various buses, and several of the components may be mounted on a common motherboard or in other manners as appropriate.

The processor 652 can execute instructions within the mobile computing device 650, including instructions stored in the memory 664. The processor 652 may be implemented as a chipset of chips that include separate and multiple analog and digital processors. The processor 652 may provide, for example, for coordination of the other components of the mobile computing device 650, such as control of user interfaces, applications run by the mobile computing device 650, and wireless communication by the mobile computing device 650.

The processor 652 may communicate with a user through a control interface 658 and a display interface 656 coupled to the display 654. The display 654 may be, for example, a TFT (Thin-Film-Transistor Liquid Crystal Display) display or an OLED (Organic Light Emitting Diode) display, or other appropriate display technology. The display interface 656 may include appropriate circuitry for driving the display 654 to present graphical and other information to a user. The control interface 658 may receive commands from a user and convert them for submission to the processor 652. In addition, an external interface 662 may provide communication with the processor 652, so as to enable near area communication of the mobile computing device 650 with other devices. The external interface 662 may provide, for example, for wired communication in some implementations, or for wireless communication in other implementations, and multiple interfaces may also be used.

The memory 664 stores information within the mobile computing device 650. The memory 664 can be implemented as one or more of a computer-readable medium or media, a volatile memory unit or units, or a non-volatile memory unit or units. An expansion memory 674 may also be provided and connected to the mobile computing device 650 through an expansion interface 672, which may include, for example, a SIMM (Single In Line Memory Module) card interface. The expansion memory 674 may provide extra storage space for the mobile computing device 650, or may also store applications or other information for the mobile computing device 650. Specifically, the expansion memory 674 may include instructions to carry out or supplement the processes described above, and may include secure information also. Thus, for example, the expansion memory 674 may be provide as a security module for the mobile computing device 650, and may be programmed with instructions that permit secure use of the mobile computing device 650. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. The instructions, when executed by one or more processing devices (for example, processor 652), perform one or more methods, such as those described above. The instructions can also be stored by one or more storage devices, such as one or more computer- or machine-readable mediums (for example, the memory 664, the expansion memory 674, or memory on the processor 652). In some implementations, the instructions can be received in a propagated signal, for example, over the transceiver 668 or the external interface 662.

The mobile computing device 650 may communicate wirelessly through the communication interface 666, which may include digital signal processing circuitry where necessary. The communication interface 666 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 668 using a radio-frequency. In addition, short-range communication may occur, such as using a Bluetooth®, Wi-Fi™, or other such transceiver (not shown). In addition, a GPS (Global Positioning System) receiver module 670 may provide additional navigation- and location-related wireless data to the mobile computing device 650, which may be used as appropriate by applications running on the mobile computing device 650.

The mobile computing device 650 may also communicate audibly using an audio codec 660, which may receive spoken information from a user and convert it to usable digital information. The audio codec 660 may likewise generate audible sound for a user, such as through a speaker, e.g., in a handset of the mobile computing device 650. Such sound may include sound from voice telephone calls, may include recorded sound (e.g., voice messages, music files, etc.) and may also include sound generated by applications operating on the mobile computing device 650.

The mobile computing device 650 may be implemented in a number of different forms, as shown in the figure. For example, it may be implemented as a cellular telephone 680. It may also be implemented as part of a smart-phone 682, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback): and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In view of the structure, functions and apparatus of the systems and methods described here, in some implementations, a systems, methods, and apparatus for identifying risk of a pregnant individual in having or developing GDM and for identifying risk of an individual in having or developing Type 2 diabetes are provided. Having described certain implementations of methods, systems, and apparatus for supporting assessment of risk of a pregnant individual in having or developing GDM and for identifying risk of an individual in having or developing Type 2 diabetes, it will now become apparent to one of skill in the art that other implementations incorporating the concepts of the disclosure may be used. Therefore, the disclosure should not be limited to certain implementations, but rather should be limited only by the spirit and scope of the following claims.

What is claimed is:

1. A method comprising:
    measuring, by immunoassay, levels of one or more biochemical markers in a blood sample obtained from a pregnant individual to determine one or more biomarker levels, wherein the one or more measured biochemical markers comprises plasminogen activator inhibitor 2 (PAI-2), wherein measuring the levels of the one or more biochemical markers comprises:
    contacting blood or a blood product from the blood sample with an anti-PAI-2 antibody that binds to PAI-2, thereby forming a complex comprising the anti-PAI-2 antibody and the PAI-2 biochemical marker, and detecting the complex in the blood or blood product from the blood sample, thereby measuring a level of PAI-2 in the blood sample;
    causing display of a graphical user interface (GUI) on a display device for entry of one or more demographic values of the pregnant individual;
    receiving, by a processor of a computing device, via the GUI, the one or more demographic values of the pregnant individual;
    accessing, by the processor, the one or more measured biomarker levels;
    identifying, by the processor, for each of the one or more measured biochemical markers, a difference between the measured biomarker level and a corresponding predetermined control level;
    determining, by the processor, a relative risk of the pregnant individual having or developing gestational diabetes mellitus (GDM) based at least in part on (i) the difference, for each biochemical marker, between the biomarker level and the corresponding control level, and (ii) the one or more demographic values of the pregnant individual;
    causing display of a graphical indication of the relative risk of the pregnant individual having or developing GDM; and
    administering to the pregnant individual medication comprising one or more members selected from the group consisting of a meglitinide, a sulfonylurea, a dipeptidy peptidase-4 inhibitor, a biguanide, a thiazolidinedione, an alpha-glucosidase inhibitor, an islet amyloid polypeptide mimetic, an incretin mimetic, and an insulin.

2. The method of claim 1, wherein the pregnant individual is within a first trimester stage of pregnancy at time of obtaining the blood sample.

3. The method of claim 1, wherein measuring the one or more biochemical markers comprises determining a concentration of each respective biochemical marker.

4. The method of claim 1, wherein measuring the one or more biochemical markers comprises determining a quantity of each respective biochemical marker.

5. The method of claim 1, wherein:
    the GUI comprises one or more biomarker level input fields for entry of the one or more measured biomarker levels, and
    accessing the one or more biomarker levels comprises receiving a user entry of each of the one or more measured biomarker levels via the GUI.

6. The method of claim 1, wherein the one or more demographic values of the pregnant individual comprises at least one of a gestational age, a weight, a body mass index (BMI), a family history status, a race, and a smoking status.

7. The method of claim 1, wherein the one or more demographic values of the pregnant individual comprise a gestational age, a patient weight, and a smoking status.

8. The method of claim 1, wherein the graphical indication of the relative risk of the pregnant individual having or developing GDM is a graphical indicator of whether the pregnant individual is positive or negative for increased risk of having or developing GDM.

9. The method of claim 1, wherein the immunoassay by which the levels of the one or more biochemical markers are measured is selected from the group consisting of enzyme immunoassay (EIA), capillary electrophoresis immunoassay (CEIA), radioimmunoassay (RIA), immunoradiometric assays (IRMA), fluorescence polarization immunoassay (FPIA), dissociation-enhanced lanthanide fluorescent immunoassay (DELFIA) and chemiluminescence assay (CL).

10. The method of claim 9, wherein the immunoassay is an enzyme immunoassay selected from the group consisting of enzyme multiplied immunoassay technique (EMIT), enzyme-linked immunosorbent assay (ELISA), IgM antibody capture ELISA (MAC ELISA), and microparticle enzyme immunoassay (META).

11. A method comprising:
    measuring, by immunoassay, levels of one or more biochemical markers in a blood sample obtained from a pregnant individual to determine one or more biomarker levels, wherein the one or more measured biochemical markers comprises plasminogen activator inhibitor 2 (PAI-2), wherein measuring the levels of the one or more biochemical markers comprises:

contacting blood or a blood product from the blood sample with an anti-PAI-2 antibody that binds to PAI-2, thereby forming a complex comprising the anti-PAI-2 antibody and the PAI-2 biochemical marker, and detecting the complex in the blood or blood product from the blood sample, thereby measuring a level of PAI-2 in the blood sample;

causing display of a graphical user interface (GUI) on a display device for entry of one or more demographic values of the pregnant individual;

receiving, by a processor of a computing device, via the GUI, the one or more demographic values of the pregnant individual;

accessing, by the processor, the one or more biomarker levels;

calculating, by the processor, a risk assessment score corresponding to a relative risk of the pregnant individual having or developing gestational diabetes mellitus (GDM), wherein the risk assessment score is based in part upon (i) a comparison of each measured biomarker level and a corresponding predetermined control level, and (ii) the one or more demographic values of the pregnant individual;

causing display of a graphical indication of the relative risk of the pregnant individual having or developing GDM; and administering to the pregnant individual medication comprising one or more members selected from the group consisting of a meglitinide, a sulfonylurea, a dipeptidy peptidase-4 inhibitor, a biguanide, a thiazolidinedione, an alpha-glucosidase inhibitor, an islet amyloid polypeptide mimetic, an incretin mimetic, and an insulin.

12. The method of claim 11, wherein:
the GUI comprises two or more biomarker level input fields for entry of the one or more measured biomarker levels, and
accessing the one or more biomarker levels comprises receiving a user entry of each of the one or more measured biomarker levels via the GUI.

13. The method of claim 11, wherein the one or more demographic values of the pregnant individual comprises at least one of a gestational age, a weight, a body mass index (BMI), a family history status, a race, and a smoking status.

14. The method of claim 11, wherein the one or more demographic values of the pregnant individual comprise a gestational age, a patient weight, and a smoking status.

15. The method of claim 11, wherein the graphical indication of the relative risk of the pregnant individual having or developing GDM is a readout of a numeric value of the risk assessment score.

16. The method of claim 11, wherein the immunoassay by which the levels of the one or more biochemical markers are measured is selected from the group consisting of enzyme immunoassay (EIA), capillary electrophoresis immunoassay (CEIA), radioimmunoassay (RIA), immunoradiometric assays (IRMA), fluorescence polarization immunoassay (FPIA), dissociation-enhanced lanthanide fluorescent immunoassay (DELFIA) and chemiluminescence assay (CL).

17. The method of claim 16, wherein the immunoassay is an enzyme immunoassay selected from the group consisting of enzyme multiplied immunoassay technique (EMIT), enzyme-linked immunosorbent assay (ELISA), IgM antibody capture ELISA (MAC ELISA), and microparticle enzyme immunoassay (META).

18. A method comprising:
obtaining a blood sample from a pregnant individual;
contacting blood or a blood product from the blood sample with an anti-plasminogen activator inhibitor 2 (PAI-2) antibody that binds to PAI-2, thereby forming a complex comprising the anti-PAI-2 antibody and PAI-2, thereby forming a complex comprising the anti-PAI-2 antibody and PAI-2, and detecting the complex in the blood or blood product from the blood sample, thereby measuring by immunoassay a level of PAI-2 in the blood sample;

causing display of a graphical user interface (GUI) on a display device for entry of one or more demographic values of the pregnant individual;

receiving, by a processor of a computing device, via the GUI, the one or more demographic values of the pregnant individual;

accessing, by the processor, the level of PAI-2 in the sample;

calculating, by the processor, a risk assessment score for gestational diabetes mellitus (GDM) based on:
(a) a decrease in the level of PAI-2 in the blood sample compared to a corresponding predetermined control level; and
(b) the one or more demographic values of the pregnant individual;

determining, by the processor, a relative risk of the pregnant individual having or developing GDM based on the risk assessment score;

causing display of a graphical indication of the relative risk of the pregnant individual having or developing GDM; and administering to the pregnant individual medication comprising one or more members selected from the group consisting of a meglitinide, a sulfonylurea, a dipeptidy peptidase-4 inhibitor, a biguanide, a thiazolidinedione, an alpha-glucosidase inhibitor, an islet amyloid polypeptide mimetic, an incretin mimetic, and an insulin.

19. The method of claim 18, wherein the immunoassay is selected from the group consisting of enzyme immunoassay (EIA), capillary electrophoresis immunoassay (CEIA), radioimmunoassay (RIA), immunoradiometric assays (IRMA), fluorescence polarization immunoassay (FPIA), dissociation-enhanced lanthanide fluorescent immunoassay (DELFIA) and chemiluminescence assay (CL).

20. The method of claim 19, wherein the immunoassay is an enzyme immunoassay selected from the group consisting of enzyme multiplied immunoassay technique (EMIT), enzyme-linked immunosorbent assay (ELISA), IgM antibody capture ELISA (MAC ELISA), and microparticle enzyme immunoassay (META).

* * * * *